United States Patent [19]

Redenbaugh

[11] Patent Number: 4,583,320
[45] Date of Patent: Apr. 22, 1986

[54] DELIVERY SYSTEM FOR MERISTEMATIC TISSUE

[75] Inventor: M. Keith Redenbaugh, Davis, Calif.

[73] Assignee: Plant Genetics, Inc., Davis, Calif.

[21] Appl. No.: 545,678

[22] Filed: Oct. 25, 1983

Related U.S. Application Data

[63] Continuation-in-part of Ser. No. 433,688, Oct. 12, 1982.

[51] Int. Cl.⁴ ............................................. A01C 1/06
[52] U.S. Cl. ........................................ 47/57.6; 47/58
[58] Field of Search ............... 47/57.6, 58; 111/1, 111/6–7

[56] References Cited

U.S. PATENT DOCUMENTS

| | | | |
|---|---|---|---|
| 2,967,376 | 1/1961 | Scott | 47/57.6 |
| 3,600,830 | 8/1971 | Hamrin | 47/57.6 |
| 3,688,437 | 9/1972 | Hamrin | 47/57.6 |
| 3,734,987 | 5/1973 | Hamrin | 47/57.6 X |
| 3,973,355 | 8/1976 | McKenzie | 47/57.6 X |
| 4,241,537 | 12/1980 | Wood | 47/57.6 X |
| 4,245,432 | 1/1981 | Dannelly | 47/57.6 |
| 4,249,343 | 2/1981 | Dannelly | 47/57.6 |

FOREIGN PATENT DOCUMENTS 33508  2/1982  Japan ................................ 47/57.6

OTHER PUBLICATIONS

Application of Plant Cell and Tissue Culture to Agriculture and Industry, Evans & Sharp, 1982, Univ. of Guelph, Ont. Can., pp. 209, 212–214.

*Primary Examiner*—Robert E. Bagwill
*Attorney, Agent, or Firm*—Limbach, Limbach & Sutton

[57] ABSTRACT

Novel methods and compositions are provided for the delivery of plant meristematic tissue to an environment for growth and development. Isolated meristematic tissue from various sources are combined with beneficial adjuvants in an encapsulating gel matrix which provides a system for the simultaneous delivery of meristematic tissue and adjuvants which can replace true botanic seed.

14 Claims, No Drawings

_4,583,320_

DELIVERY SYSTEM FOR MERISTEMATIC TISSUE

RELATED APPLICATION DATA

This application is a continuation-in-part of copending application Ser. No. 433,688, filed Oct. 12, 1982.

DESCRIPTION

1. Technical Field

This invention relates generally to the field of agriculture and crop production and more particularly to the delivery of improved crop varieties together with substances which enhance their growth and development.

2. Background of the Invention

The conventional techniques of crop and plant delivery in agriculture include placing seed directly in the ground either by hand or machine planting. Either of these techniques may be incorporated in a broadcast or precision sowing method. Such seed is commonly planted untreated or sometimes treated to a brief dip in a fungicide or covered with a layer of dry diatomaceous earth (or other appropriate material) with or without dried preparations of microorganisms.

As an alternative, such seeds, treated or untreated, are first sown in greenhouse or nursery beds. Plantlets are raised to a particular size before transplanting to the field. Conventional methods of seed planting and transplant production are well known and described in the literature. See, e.g., J. H. Martin and W. H. Leonard, "Principles of Field Crop Production," (Macmillan Company, N.Y., 1949); J. H. MacGillivray, "Vegetable Production," (Blakiston Co., N.Y., 1953); and R. L. Carolus, "Possibilities with the Use of Pelleted Seed" (Ohio Veg. and Potato Growers Assoc., Ann. Proc. 34: 56062, 1949).

The conventional technique of delivery of adjuvants that affect plant, insect, fungus, bacteria, animal and other growth is to apply the adjuvant physically separate from the plant seed. Plant Nutrients, pesticides, beneficial microorganisms and other biologically active compounds are applied (1) before the time of seed planting by soil incorporation or by placement on top of the soil, (2) to the soil as the seeds are being planted, or (3) after the seeds are planted by soil incorporation, spray application, or other physical means. Conventional methods are well known and described in the literature. See, e.g. J. Janick, R .W. Schery, F. W. Woods, V. W. Ruttan, "Plant Science," (W. H. Freeman, San Francisco, 1974); and "Western Fertilizer Handbook," (Institute Printers and Publishers, Danville, Ill., 1975).

A major limitation to these conventional methods is the requirement to plant the seeds and deliver the adjuvants separately, usually by way of separate passes through the field with the tractor. This is both costly and increases the incidence of soil compaction due to the tractor weight.

An additional limitation is that the adjuvant is not precision applied to the specific points in the field where the adjuvant reacts. For beneficial microorganisms, this application point is at the seed where developing roots will interact with the microorganisms. The same application point is required for herbicides to limit weed competition, nematicides to control root invading nematodes, insecticides to control both root and upper plant-attacking insects, nutrients to nourish the developing plant, as well as other adjuvants to benefit crop establishment and growth. Because adjuvant application by conventional methods is non-precise much of the adjuvant is wasted or non-effective.

A further limitation is that many adjuvants are volatile, flammable, toxic or otherwise environmentally hazardous, and therefore, pose difficulty in handling and application for both the operator and the environment.

It has been recognized that some of these difficulties may be overcome by incorporating some of the adjuvants, specifically micro-organisms, in a dry covering around the seed. See, e.g., T. V. Suslow and M. N. Schroth (Phytopathology 72: 199, 1982). This technique provides for direct application of microorganisms with the seed. However, the process to coat the seed requires that both the seeds and microorganisms be dried, a process that often results in decreased seed germination rates and death of a majority of the microorganisms.

Another technique which has found some use is fluid drilling. Pre-germinated seeds are delivered, occasionally with microorganisms or other additives, in a thick slurry by means of special implements. See, e.g. Taylor, J. D. and C. L. Dudley, "Rhizobium Inoculation of Dwarf Beans", Nat. Veg. Res. Sta. U.K. 28th Ann. Rep. p. 105 (1977); Hardaker, J. M. and R. C. Hardwick, "A Note on Rhizobium Inoculation of Beans", Expl. Agric. 14:17-21 (1978); Entwistle, A. R. and H. L. Munasinghe, "The Control of White Rot (_Sclerotium cepivorum_) in Fluid-drilled Salad Onions" J. Hort. Sci. 56:251-54 (1981). However, this method does not permit precise seed planting, seed viability is often reduced, and specialized planting equipment is required.

It has been suggested that adjuvants be microencapsulated to provide controlled release of the adjuvants, thereby lengthening the time of activity. See, e.g., T. J. Roseman and S. Z. Mansdorf, "Controlled Release Delivery Systems" (Marcel Dekker, Inc., N.Y., 1983). However, this technique does not provide for precision placement of the adjuvants where they will be most effective.

Thus, an object of this invention is to provide a technique whereby meristematic tissue is advantageously combined with adjuvants prior to planting.

Another object of this invention is to control germination and development of the meristematic tissue.

Yet another object of the invention is to provide a medium to deliver the meristematic tissue together with adjuvants.

A further object of the invention is to reduce the amount of handling and time required for delivery of meristematic tissue and adjuvants to field, nursery, or greenhouse.

A still further object of the invention is to provide a delivery method of meristematic tissue and adjuvants.

A final object of the invention is to control the release of the meristematic tissue and adjuvants.

DISCLOSURE OF THE INVENTION

Method and compositions are provided for the delivery of meristematic tissue and beneficial adjuvants to an environment for growth and development wherein meristematic tissue with the potential to produce an entire plant body is isolated and encapsulated together with an effective concentration of at least one adjuvant capable of effecting the meristematic tissue, the resulting plant body or their environment.

BEST MODE FOR CARRYING OUT THE INVENTION

In accordance with the invention, methods and compositions are provided for delivering meristematic tissue and beneficial adjuvants as a unit by encapsulating these components in a gel. Botanic seed contains meristematic tissue which has the potential to differentiate and produce an entire plant body. Also included with the meristematic tissue in botanic seed are various accessory structures and compounds which promote the development and survival of the plant and which function to impede the progress of competitors.

Plant meristematic tissues are units of organization. Some meristematic tissues have the capacity to produce an entire plant body; others produce only selected tissues. Those which produce an entire plant body are termed totipotent. It is an inherent property of an embryo to recapitulate ontogeny. This capacity resides in the meristem, and the other structures in a seed or embryo are accessory to this meristematic tissue.

Botanic seed can be encapsulated in accordance with the present invention to provide the necessary meristematic tissue. Meristematic tissue, termed totipotent, can also be isolated from many sources, including the induced formation of such tissue from the somatic tissue of a plant.

The accessory structures and compounds normally included with meristematic tissue can be substituted or supplemented by various adjuvants including microorganisms and biologically active compounds which will modify the plant or its environment to enable the tissue to thrive and compete more successfully for resources. These various adjuvants can be mixed together in a homogeneous solution and subsequently gelled. Alternatively, the components can be injected into a preformed gel or layered onto a core (containing for example meristematic tissue) to build up a multi-layered capsule with components arranged in a specific order for delivery and release. As an additional alternative, the various components of the capsule can be microencapsulated or otherwise treated to impede or control release of the components as well as to protect components from other adjuvants or materials within the capsule.

In accordance with the invention, meristematic tissue and adjuvants are combined for delivery by encapsulating the components in a gel which can control germination and development of the meristematic tissue as well as the release and function of the adjuvants.

Selection of Meristematic Tissue

Botanic seed is a means which has evolved to deliver the progeny of plants to sites which are suitable for development and growth. The essential element of botanic seed is the meristematic tissue which differentiates to form an entire plant body.

Botanic seed is readily available from most plant and crop species. Seed production methods are well known to the industry. See, e.g., J. Janick, R. W. Schery, F. W. Woods, V. W. Ruttan, "Plant Science" (W. H. Freeman, San Francisco, 1974); and H .T. Hartmann and D. E. Kester, "Plant Propagation" (Prentice-Hall, Englewood Cliffs, N.J., 1975). Thus any available botanic seed can be encapsulated in accordance with the present invention.

Cultured plant tissue can be isolated from numerous sources, including somatic tissue, zygotic tissue or germ line tissue. Regardless of its source, the tissue must pass through a meristem stage in order to undergo organogenesis and develop into a regenerated plant body.

Somatic tissue sources which are not ordinarily involved in reproduction can, under appropriate circumstances of inducement, form meristematic tissue.

As a first step in the production of encapsualted somatic embryos, crop strains must be selected which are capable of somatic embryogenesis. For a representative list of such species see D. A. Evans and D. R. Sharp, "Application of Tissue Culture Technology in the Agricultural Industry," in Application of Plant Cell and Tissue Culture to Agriculture and Industry, D. T. Tomes et al., editors, (University of Guelph Press, page 214, 1982). Further species may be shown capable of somatic embryogenesis with further experimentation and refinement of technique.

Once the appropriate strain is selected, preparation of somatic embryos can proceed by any of numerous known techniques. For example, in alfalfa, see K. A. Walker and S. J. Sato, "Morphogenesis in Callus Tissue of *Medicago sativa:* the Role of Ammonium Ion in Somatic Embryogenesis," Plant Cell Tiss. Org. Cult. 1: 109–121 (1981). For other techniques known to the art see e.g. Street, H. E., ed., "Plant Tissue and Cell Culture," University of California Press (1977).

The somatic tissue of certain other species are able to undergo shoot organogenesis without the intermediate formation of somatic embryos. See, T. Murashige, "Plant Propagation Through Tissue Culture," Ann. Rev. Plant Physiol. 25: 135–146 (1974). Tissue from these plants may be encapsulated without the preliminary embryogenesis step, and mature plants grown therefrom.

As an alternative, zygotic embryos can be used when for example the species is incapable of somatic embryogenesis. These zygotic embryos can be grown in culture or suspension, and then be encapsulated with or without their seed coat and other accessory structures.

In certain wide crosses, a fertile embryo is formed but the endosperm fails to develop and the embryo then dies. Thus the cross appears sterile, but viable progeny can be obtained by isolating the embryo from the aborted ovule. The zygotic embryos may be separated from their seed coat and then encapsulated with adjuvants which will enhance their growth and viability. See for example M. Monnier, "Culture of Zygotic Embryos," Frontiers of Plant Tissue Culture, T. A. Thorpe, ed. (The International Association for Plant Tissue Culture, University of Calgary, Alberta, Canada p. 277–280, 1978).

Encapsulation Media—Gels

It has been recognized that the germination and development of seeds may be enhanced by coating them with various materials. For example, it has been reported that coating seeds with Super Slurper (USDA) will result in a water-absorbent reservoir which improves the germination rate in arid conditions.

It has been demonstrated that perishable foods may be preserved by coating them with a complexed carbohydrate, e.g. Earle U.S. Pat. No. 3,395,024. There are also reports of seeds coated with dried materials, using e.g. alginate as a binding compound, U.S. Pat. Nos. 3,545,129 and 3,698,133; Dexter, S. T. and T. Miyamoto, Agron J., 51:338 (1959).

The meristematic tissue can be encapsulated in accordance with the present invention in any of numerous media which provide an appropriate encapsulation matrix, hereafter termed "gel." In general, a gel will allow meristem or embryo respiration by permitting diffusion of gases. The gel should provide a capsule strong enough to resist external abrasion and adverse forces, yet pliable enough to allow the growth of the embryo and its germination at the appropriate time. Gels finding use in the present invention are preferably, but not exclusively, hydrogels, which contain water within the confines of the gel matrix. It may be desirable to use various gels in combination, either as a mixture or in layers, to achieve the desired results.

Gels which have been found useful for encapsulating meristematic tissue include sodium alginate, guar gum, carrageenan with locust bean gum, and sodium alginate with gelatin. Other suitable gels include, but are not limited to:

TABLE 1. GEL AGENTS

I. Natural Polymers
  A. Ionic bonds (requires complexing agents)
    Alginate with Gelatin
    Sodium Pectate
    Furcellaran
    Pectin
    Hypnean
    Dextran
    Tamarind
    Guar Gum
  B. Hydrophobic Interactions
    Amylose
    Agar
    Agarose
    Agar with Gelatin
    Gelatin
    Starch
    Amylopectin
    Cornhull Gum
    Starch Arabogalactan
    Gum Ghatti
    Gum Karagan
    Ti Gum
    Gum Tragacanth
    Wheat Gum
    Chitin
    Dextrin
II. Chemically Modified Natural Polymers
  A. Ionic bonds (requires a complexing agent)
    Ethyl Succinylated Cellulose
    Succinylated Zein
    Carboxymethylcellulose
  B. Hydrophobic Interactions
    Methylcellulose
    Hydroxyethyl Cellulose
  C. Covalent Bonds
    Gelatin with Glutaraldehyde
III. Synthetic Polymers
  A. Covalent Bonds
    Polyacrylamide
  B. Hydrophobic Interactions
    Polyethylene Glycol
    Polyvinylpyrrolidone
    Polyoxyethylene
    Hydrophilic Urethane
    Polyvinylacetate
    Vinyl Resins
    Hydron (hydroxyethylmethacrylate)
    2-methyl-5-vinylpyridinemethylacrylate-methacrylic acid
  C. Ionic Bonds
    Sodium poly (styrene sulfonate) with poly(vinyl methyl pyridinium) chloride
    Sodium poly (styrene sulfonate) with poly (vinyl benzyl trimethyl ammonium) chloride
    Strongly acidic polyanion with strongly basic polycation
    Bordon Poly Co. 2113 ® (vinyl acetato homopolymer) (Bordon Co.)
    Gelvatol ® (polyvinyl alcohol resin)(Monsanto)
IV. Stabilizing Compounds
  A. Trade Names
    Super Slurper ® (USDA, SEA-AR, Nor. Reg. Res. Lab)
    Viterra ® (Union Carbide)
    Laponite ® (Laporte (United States) Inc.)
    Gelrite ® (Kelco)
    SeaKem ® (FMC Corporation)
    SeaPlaque ® (FMC Corporation)
    SeaPrep ® (FMC Corporation)
    IsoGel ® (FMC Corporation)
  B. Organic Compounds
    Methylan Clear Wallpaper Paste
    Lactose
    Wax
    Protein Colloids
  C. Inorganic Compounds
    1. Clay
    2. Compounds that adhere by means of a water water-soluble plastic such as methylcel:
      Fly Ash
      Feldspar
      Celrite
      Bentonite
      Vermiculite
      Diatomaceous Earth
      Lime
      Calcium Carbonate
    3. Other
      Calcium Oxide
      Magnesium Carbonate
      Sodium bicarbonate
      Urea Selecting Optimum Gels A gel chosen for encapsualtion would usually include the following characteristics (although the invention may be practiced in other modes):

1. A compliance adequate to protect and cushion the meristem;

2. The interior material would have solubility or emulsion forming characteristics such that it can accept and contain adjuvants, including but not limited to aqueous or hydrophobic substances;

3. An outer surface to provide a protective barrier to mechanical stress, facilitate handling and maintain meristem viability;

4. Sufficient gel strength to maintain capsule integrity, but still allow the meristem to break out during germination and for the adjuvants to be released.

Selection of Adjuvants

It has been recognized that plant establishment, growth and development may be enhanced by addition of adjuvants to the soil, to the rhizosphere of the plant, and to the surface of the plant. It has also been demonstrated that controlled release of the adjuvants may provide additional enhancement to plant growth, e.g. T. J. Roseman and S. Z. Mansdorf "Controlled Release Delivery Systems," (Marcel Dekker, Inc., N.Y., 1983).

Adjuvants which have been found to be useful for encapsulation with meristematic tissue include pesticides (bensulide, EPTC, metribuzin, pebulate, prometryn, pronamide, chlorpropham, alachlor, and diazinon), fertilizers (superphosphate, calcium phosphate, potassium phosphate, potassium nitrate, calcium nitrate and ammonium nitrate) energy sources (starch and sucrose) and microorganisms (*Rhizobia meliloti, R. leguminosarum, Azospirillum, Bacillus thuringiensis* and *Eschericia coli*).

Other suitable adjuvants include, but are not limited to:

TABLE 2. ADJUVANTS

- I. Pesticides
  - A. Herbicides
    - 1. Phenoxy compounds
      - 2,4-D
      - MCPB
      - 2,4,5-T
      - Bifenox
    - 2. Benzoic, acetic acids and phthallic compounds
      - chloramben
      - dicamba
      - bromoxynil
      - chlorthiamid
    - 3. Dinitro analines, nitrites, amides, acetamides and anilides
      - Trifluralin
      - Benefin
      - Oryzalin
      - Quinonamid
    - 4. Carbamates
      - Butylate
      - Asulam
      - Thiobencard
    - 5. Heterocyclic Nitrogen derivatives
      - Picloram
      - Aminotriazole
      - Paraquat
      - Simazine
    - 6. Urea compounds
      - Diuron
      - Bromacil
      - Terbacil
      - Isoproturon
    - 7. Metal Organics and Inorganics
      - DSMA
    - 8. Other Herbicides
      - Petroleum oils
      - Aromatic oils
      - Oxyfluorfen
      - Bentazon
      - Fluridome
  - B. Insecticides
    - 1. Cyclo Compounds
      - Endrin
      - Heptachlor
      - Lindane
      - Mirex
    - 2. Carbamate
      - Carbofuran
      - Isoprocarb
    - 3. Animal Plant Derivation and Inorganic Compounds
      - Rotenone
      - Thiocyclam
    - 4. Diphenyl Compounds
      - DDT
      - Methoxychlor
      - Difluron
      - Amitraz
    - 5. Organic Phosphates
      - Dicrotophos
      - Parathion
      - Malathion
      - Phorate
      - Phosmet
      - Penncap M ® (Pennwalt Corp.)
      - KnoxOut 2FM ® Pennwalt Corp.)
  - C. Fungicides
    - 1. Inorganics
      - Copper sulfate
    - 2. Metal Organics
      - Cadminate (Mallinckrodt Chemical Works)
    - 3. Antibiotics and Bacteriocins
      - Streptomycin
      - Cycloheximide
      - Piomy
    - 4. Carbamates
      - Ferbam
      - Ziram
      - Thiram
    - 5. Organic Fungicides
      - Carboxin
      - Captan
      - Chloroneb
      - Benomyl
      - Metalaxyl
  - D. Fumigants, Repellents and Rodenticides
    - 1. Fumigants
      - Methyl bromide
      - Carbon bisulfide
      - Propylene dichloride
      - Vapam
    - 2. Repellents
      - Thiram
      - Protect
    - 3. Rodenticides
      - Warfarin
      - Endrin
- II. Fertilizers and Nutrients
  - Nitrogen
  - Phosphate
  - Potassium
  - Sulfur
  - Calcium
  - Magnesium
  - Amino acids
- III. Energy Sources
  - Sugars
  - Carbohydrates
  - ATP
- IV. Microorganisms
  - Azospirillum species
  - Pseudomonas species
  - Azotobacter species
  - Cyanobacteria
  - *Bacillus thuringiensis*
  - Mycorrhizal fungi
  - Rhizobia species

*Bacillus subtilis*
*Bacteroides ruminicola*
*Lachnospira multiparus*
*Aspergillus fumigates*
*Fusarium oxysporum*
Paecilomyces species
Flavobacterium species
Achromobacter species
Aspergillus species
Arthobacter species
Actinomycete species
Halophytic bacteria
Nitrosomonas species
Nitrobacter species
Sulfur mineralizing bacteria
Baculovirus species
*Heliothis zea* NPV
*Autographa californica* NPV V. Growth Regulators and Hormones
  Giberellic acid
  Cytokinins
  Ethoxyquin
  Naphthalene acetic acid
  Indolebutyric acid
  para-chlorophenoxyacetic acid
  Ethylene
  Indole acetic acid VI. Other Biologically Active Components
  Denitrification inhibitors
  Iron chelators
  Pheromones
  Enzymes
  Pesticide Antidotes and Safeners VII. Other Inert Components
  Soil and water conditioners
  Dispersants
  Wetting agents
  pH altering compounds

Encapsulation with Selected Gel

Once the gel has been chosen, there are numerous parameters which influence the characteristics previously mentioned.

A sodium alginate solution, for example, will form a gel when a complexing agent is added. Calcium chloride ($CaCl_2$) is generally used, however, lanthanum chloride, ferric chloride, cobaltous chloride, calcium nitrate, calcium hydroxide, superphosphate fertilizer, and many pesticides such as benefin, alachlor and chlorpropham are also acceptable, as are other compounds generally with multivalent cations.

A chosen gel will have a range of concentrations usable in working the invention. A concentration should be chosen to optimize ease of handling, gelling time, strength of gel and coating thickness around the meristematic tissue. If the gel is too dilute, the tissue may settle during gel formation and produce an uneven encapsulation. The sodium alginate for example can be prepared in a concentration of 1 to 10% w (in grams)/v (in milliliters) in water, more usually 2 to 10% and preferably from 3 to 5%.

The meristematic tissue to be encapsulated can then be added to the sodium alginate solution at a concentration of 1 to 50 meristems per milliliter, more usually from 5 to 20 meristems per milliliter. This concentration will vary as the appropriate size of meristematic tissue varies with species, source and stage of development.

Specific adjuvants to be encapsulated can then be added to the sodium alginate and meristem solution at concentrations specific for the application rates of the particular adjuvants. Pesticides for example can be added at a concentration of 0.0002 to 2.0000 milliliters formulated pesticide ($2 \times 10^{-6}$ to 2 grams active ingredient) per milliliter sodium alginate solution, more usually from 0.002 to 0.200 milliliters formulated pesticide ($2 \times 10^{-4}$ to 0.18 grams active ingredient) per milliliter. Fertilizers for example can be added at a concentration of 0.1 to 200 milligrams per milliliter sodium alginate. Microorganisms for example can be added at a concentration of 1 to $10^{12}$ microorganisms per milliliter sodium alginate, more usually $10^4$ to $10^{10}$ microorganisms per milliliter. Carbon sources can be added at a concentration of 1 to 500 milligrams per milliliter of sodium alginate solution, more usually 5 to 100 milligrams per milliliter.

The dispersed adjuvants and meristematic tissue in gel solution can then be added dropwise to the complexing agent. Alternatively, the gel solution and complexing agent may be mixed by any of numerous techniques known to the art. These may include droplet formation and agent addition as a one step process by a vibrating nozzle which ejects a gel droplet from one source and coats the droplet with complexing agent from another.

The calcium chloride (or other complexing agent) can be made up in solution at a concentration of 1 to 1,000 millimolar, more usually 20 to 500 millimolar and ideally from 50 to 300 millimolar. Other complexing agents will have different preferred concentration ranges.

The time for gel formation and the temperature of the gelling solutions are interrelated parameters, for selected concentrations of gel and complexing agent. The temperature should be chosen so as to aovid damage to the meristematic tissue, usually in the range of 1° to 50° C., more usually 10° to 40° C., and preferably at 20° to 40° C.

Within the range of acceptable temperatures, a particular value can be chosen to give the shortest possible gelling time consistent with complete gel formation. Typically, the gel will form immediately, but the complexation takes much longer. For a solution of sodium alginate at a concentration of 3.2 grams per 100 milliliters $H_2O$, 0calcium chloride solution concentration of 50 millimolar and 25° C. reaction temperature, adequate gelling is obtained in 5 to 120 minutes, more often 10 to 90 minutes and is usually sufficiently complete in 30 to 60 minutes. Alternatively, if 300 millimolar calcium chloride is substituted for 50 millimolar calcium chloride, gelation time is decreased to 2–5 minutes.

The gel characteristics described above are modifiable for each gel, but are determined generally by the concentration parameters and chemical properties of the gel.

Further Modifications

In agricultural applications, it is generally preferred that harvesting be accomplished in a brief period of time and in the appropriate season. Therefore, either before or during the gelling process, it may be desirable to synchronize the germination of the meristems or embryos through techniques known to the art, such as the use of mitotic blockers or sizing through sieves, so that any given batch of encapsulated meristems, somatic embryos or seeds will germinate at approximately the same time.

Various salts may be used to control and impede meristem germination, particularly osmotically active monovalent salts. For example, sodium chloride, at concentrations of 0.1 to 1.0 molar, more usually 0.3 to 0.6 molar, will control germination of tomato seeds inside calcium alginate capsules. This germination control was effective for at least one month when encapsulated tomato seeds with salt are stored in a sealed container. Upon placement in agar water or in soil, the seeds readily and uniformly germinated at rates equal to controls that contained no salt or that were not encapsulated.

As an alternative to tomato, lettuce or petunia can be similarly treated for germination control.

As an alternative, potassium nitrate can replace sodium chloride at the same concentrations. Potassium nitrate has an additional effect on encapsulated seeds, being a fertilizer source of both potassium and nitrogen.

High osmotic potentials will also control meristem germination. For example, sucrose at concentrations of 6 to 20% weight in grams per water in liters, more usually 8 to 15%, and ideally 10 to 14% will control germination of Brassica zygotic embryos isolated from immature seeds when encapsulated inside calcium alginate capsules. This germination control was effective for at least one month when the encapsulated Brassica embryos and sucrose were stored in a sealed container. Upon placement on Schenk and Hildebrandt medium (SH) (Can. J. Bot. 50:199-204, 1972) the embryos readily and uniformly germinated at rates equal to controls.

As an alternative to salts or sucrose, abscisic acid affects seed germination. For example, abscisic acid at concentrations of $10^{-3}$ to $10^{-6}$ molar, more usually $10^{-4}$ to $10^{-5}$ molar, will similarly control Brassica embryo germination.

As another alternative, storage of encapsulated seeds or embryos at low temperatures, 0° to 10° C., more usually 2° to 8° C. in conjunction with any of salts, sucrose or abscisic acid will also control embryo germination.

Subsequent to encapsulation or planting, it may be desirable to store the encapsulated meristematic tissues, transport them to the field, hothouse or the nursery, and treat them in a manner consistent with botanic seed. Planting these encapsulated meristematic tissues can be accomplished in the nursery or hothouse for species unable to tolerate the ambient climatic conditions without some period of acclimization. Alternatively, for more hardy species, the encapsulated meristems may be planted directly in the field through numerous techniques employed in the art for botanic seed.

Experimental

In order to demonstrate the invention, the following experiments were carried out with a variety of meristematic tissue material, gel media and adjuvants. All quantities labelled percent (%) are grams per 100 milliliters, unless otherwise indicated.

EXAMPLE A (tomato seeds)

1. Encapsulation with Bensulide (Prefar)

Tomato seeds, Campbell 28, lot #2271-156 (A. Castle Co., Inc.), were adjusted to a concentration of 80 seeds per 10 milliliters of 3.2% sodium alginate at 25° C. To this mixture was added 0.2 milliliters of bensulide (0,0-diisopropyl phosphorodithiioovate-S-ester with N-(2-mercaptoethyl) benzenesulfonamide), a plant herbicide. The mixture was stirred into a slurry and and then dispensed dropwise from a 5 milliliter Pipetman pipette into 50 milliliters of 100 millimolar calcium chloride at 25° C. At these concentrations, capsules formed immediately, but the complete complexation required 20 to 60 minutes. At this point, the calcium chloride solution was poured off and the capsules containing tomato seeds and bensulide were collected.

The capsules were planted in aluminum trays (8 inches by 12 inches) containing two inches of a soil mixture consisting of sand, sphagnum peat moss, fir bark, calcium nitrate, urea formaldehyde, superphosphate, calcium carbonate lime, dolomite and iron sulfate. The capsules were placed in a row $\frac{1}{4}$ inch deep parallel to the long axis of the aluminum tray and covered with the soil mixture. Weed seeds (barnyard grass, pigweed, wild mustard, crabgrass, wild oats and lamb's quarter) were then spread in parallel rows perpendicular to the row of capsules. The trays were placed in a greenhouse and watered when the soil dried.

Using the above protocol, tomato seed germination rates of 120 to 156% over the controls were achieved. The tomato plants grown from herbicide encapsulated seeds were equal in height, color and leaf size and shape to the controls. One set of controls were tomato seeds treated as described in the above protocol with the omission of the bensulide. A second set of controls consisted of tomato seeds that were not encapsulated or treated with the bensulide, but were otherwise treated as described in the above protocol.

Weed seed germination was inhibited within a narrow zone bounded by the width of the row above the encapsulated tomato seeds. All six weed species were affected by the herbicide.

1A. As an alternative herbicide concentration, 0.02 milliliters of bensulide can replace the 0.2 milliliters of bensulide in the protocol of A.1. Tomato seed germination rates were 127 to 179% over the controls but little weed control was evident.

2. Encapsulation with EPTC (Eptam)

The experimental protocol A.1. was duplicated, substituting EPTC (S-ethyl dipropylthiocarbamate) at a concentation of 0.2 milliliters per 10ml sodium alginate for bensulide. Tomato seed germination rates were 150 to 159% over that of the controls. The tomato plants were equal in height, color, and leaf size and shape to the controls. Weed control differed from that of protocol A.1 in that the zone of weed inhibition was extended to 1 inch from either edge of the row of encapsulated tomato seeds.

2a. As an alternative herbicide concentration, 0.02 milliliters of EPTC can replace the 0.2 milliliters of EPTC in the protocol of A.2. Tomato seed germination rates of 123 to 194% over the controls were achieved with similar results as described in protocol A1.

2b. As an alternative herbicide concentration, 0.002 milliliters of EPTC can replace the 0.2 milliliters of EPTC in the protocol of A2. Tomato seed germination rates of 147% over the controls was achieved. Tomato plant quality was the same as described in protocol A2. Weed control was the same as described in protocol A2, but only for wild mustard, crabgrass and lamb's quarter.

3. Encapsulation with Metribuzin (Lexone)

The experimental protocol of A1 was duplicated, substituting Metribuzin (4-amino-6-(1,1-dimethylethyl)-3-(methylthio)-1,2,4-triazin-5(4H)-one) at a concentration of 0.002 milliliters per 10 ml sodium alginate for bensulide. Tomato seed germination rate was 118% over that of the controls. The tomato plants were reduced in size as compared to the controls. Weed control was the same as in protocol A.1, except that only wild mustard and lamb's quatter seeds were controlled.

4. Encapsulation with Pebulate (Tillam)

The encapsulation protocol of A1 was duplicated, substituting pebulate (S-propyl butylethylthiocarbamate) at a concentration of 0.02 milliliters per 10 ml sodium alginate for bensulide. Tomato seed germination rate was 108% over that of the controls. The tomato plants were equal in height, color, and leaf size and shape to the controls. Weed control was the same as described in Protocol A1 except that only crabgrass and wild oats were controlled.

5. Encapsulation with Diphenamid

The encapsulation protocol of A1 was duplicated substituting diphenamid (N,N-dimethyl-2,2-diphenylacetamide) at a concentration of 4 mg per 10 milliliters sodium alginate for bensulide. Tomato seed germination rate was 100% over that of the controls the tomato plants were equal in height, color, and leaf size and shape to the controls. Weed control was the same as described in Protocol A2 except that only crabgrass and lamb's quarter were controlled.

EXAMPLE B (Celery)

1. Celery Seeds

Celery seeds, Florida 683 lot #11621-12526 (Ferry Morse Co.), were encapsulated as described in protocol A1 with the exception of substituting .002 milliliters of EPTC per 10 ml sodium alginate for bensulide. Celery seed germination rate was 147% over that of the controls. The celery plants were equal in height, color, and leaf size and shape to the controls. Weed control was the same as described in protocol A2 except that only wild mustard, crabgrass and lamb's quarter were controlled.

2. Celery Somatic Embryos

As an alternative to celery seeds in B1, celery somatic embryos obtained by conventional techniques can be encapsulated with 0.02 to 0.20 milliliters of chlorpropham. When the encapsulated embryos are placed on Schenk and Hildebrandt nutrient medium (Can. J. Bot. 50: 199–204, 1972), the somatic embryos germinate and shoots and roots are produced.

2.a. As an alternative, formulated prometryn (2,4-bis-(isopropylamino)-6-(methylthio)-5-triazine) can be substituted for chlorpropham.

2.b. As an alternative technical prometryn can be substituted for formulated prometryn.

Example C (Lettuce)

Lettuce seeds, Salinas GH-11 (Moran) were encapsulated as described in protocol A.1 with the exception of substituting 0.002 to 0.020 millimeters of pronamide (3,5-dichloro-N-(1,1-dimethy-1-2-propynyl)benzamide) per 10 ml sodium alginate for bensulide. Lettuce seed germination rates were 78 to 86% of that of the controls. The lettuce plants were equal in height, color, and leaf size and shape of the controls.

Example D (Brassica)

1. Encapsulation with Trifluralin (Treflan) Brassica, PHW Ccc-1 (Dr. Paul H. Williams, University of Wisconsin), zygotic embryos isolated from immature seeds were encapsulated as described in protocol A.1 with the exception of substituting 2 to 100 microliters of trifluralin ($\alpha,\alpha,\alpha$-trifluoro-2,6-dinitro-N,N-dipropyl-p-toluidine) and sowing the capsules on 0.8% w/v agar water. Seed germination rates were 80 to 95% of the controls. The Brassica plants were equal in height, color, and leaf size and shape to the controls.

2. Encapsulation with Bensulide

The experimental protocol D.1 was duplicated substituting bensulide at concentrations of 2 to 10 microliters for trifluralin. Seed germination rates were 90 to 113% of the controls and the plants were equal in height, color, and leaf size and shape to the controls. Weed seed germination was inhibited for wild mustard, lamb's quarter and pigweed.

Example E (Alfalfa)

1. Encapsulation with an Insecticide/Fungicide

Alfalfa seeds, Saranac AR Lot #27-07-765 (Whitney Dickerson Seed Growers, Homedale, ID), were encapsulated as described in protocol A.1 with the exception of substituting 0.02 milliliters of diazinon (0,0-diethyl 0-(2-isopropyl-4-methyl-6-pyrimidinyl) phosphorothiote) at a concentration of .02 milliliters per 10 milliliters of sodium alginate for bensulide. Alfalfa seed germination rate was 78% of the control. The alfalfa plants were equal in height, color, and leaf size and shape to the controls. No weed seeds were tested.

2. Encapsulation with an Insecticide/Fungicide and a Herbicide

As an alternative combination of pesticides, 0.02 to 0.20 milliliters of diazinon and 0.002 to 0.020 milliliters of EPTC were mixed with 10 milliliters of sodium alginate and encapsulated with alfalfa seeds as in protocol E.1. Alfalfa seed germination rates were 78 to 85% of the controls. The alfalfa plants were equal in height, color, and leaf size and shape to the controls. Weed control was the same as in protocol A.1, except that only wild mustard and crabgrass were controlled.

3. Encapsulation with Sodium Alginate and Gelatin

As an alternative gel matrix to protocol E.1, 2.0% sodium alginate and 5% gelatin were mixed with 0.01 milliliter chlorpropham (isopropyl m-chlorocarbanilate) and 80 alfalfa seeds. The mixture was dropped into 50 milliliters of 100 millimolar solution of calcium chloride. Solid, intact, spherical capsules were recovered.

4. Encapsulation with Carrageenan and Locust Bean Gum

As an alternative gel matrix to protocol E.1, .40% carrageenan and 0.40% locust bean gum were mixed with 0.10 milliliters of EPTC and 80 alfalfa seeds. The mixture was dropped into 50 milliliters of 300 millimolar solution of potassium chloride. Solid, intact, spherical capsules were recovered.

5. Encapsulation with Agar

As an alternative gel matrix to protocol E.1, 5.0% agar was used to make capsules by complexation with 100 millimolar tannic acid.

6. Encapsulation with Carboxymethylcellulose

As an alternative gel matrix to protocol E.1, 2.50% carboxymethylcellulose was used to make capsules by complexation with either 100 millimolar copper sulfate or 50 millimolar aluminum sulfate.

7. Encapsulation with Gum Tragacanth

As an alternative gel matrix to protocol E.1, 2.5% gum tragacanth was used to make capsules by complexation with 100 millimolar calcium chloride.

8. Encapsulation with Sodium Pectate

As an alternative gel matrix to protocol E.1, 2.0% sodium pectate was used to make capsule by complexation with either 100 millimolar calcium chloride or 100 millimolar copper sulfate.

9. Encapsulation with Bordon Polyco 2113 ®

As an alternative gel matrix to protocol E.1, liquid Borden Polyco ® 2113 (vinyl acetate homopolymer) was used to make capsules by complexation with 100 millimolar tannic acid.

10. Encapsulation with Benefin as a Complexing Agent (Balan)

As an alternative complexing agent to protocol E.1, benefin (n-butyl-N-ethyl-$\alpha,\alpha,\alpha$-trifluoro-2,6-dinitro-p-toluidine) can be substituted for 100 millimolar calcium chloride. Ten milliliters of 3.2% sodium alginate containing alfalfa seeds were dropped into formulate benefin. Solid, flat hard capsules were recovered.

11. Encapsulation with Alachlor as a Complexing Agent (Lasso)

As an alternative complexing agent, alachlor (2chloro-2,6-diethyl-N-(methyoxymethyl)acetanilide) can be substituted for benefin as a complexing agent for sodium alginate as described in protocol E.10.

12. Encapsulation with Chlorpropham as a Complexing Agent (Furloe)

As an alternative complexing agent, chlorpropham can be substituted for benefin as described in protocol E.10.

13. Encapsulation with Superphosphate as a Complexing Agent

As an alternative complexing agent, superphosphate fertilizer in concentrations of 50-400 milligrams per 20 milliliters of water can be substituted for calcium chloride as in E.10.

EXAMPLE F (Nutrient Encapsulation)

Tomato seeds were encapsulated as described in protocol A.1 with the exception that potassium phosphate was added as a fertilizer to the alginate mix at concentrations of 4 to 200 milligrams per 5 milliliters of sodium alginate rather than adding a herbicide for weed control. Tomato seed germination rates were comparable to those of the controls.

1.a. As an alternative to potassium phosphate, calcium phosphate at concentrations of 5 to 200 milligrams can be added to the alginate mix as a fertilizer.

1.b. As an alternative to potassium phosphate, starch at concentrations of 25 to 500 milligrams can be added to the alginate mix as a carbon source.

1.c. As an alternative to potassium phosphate, ammonium nitrate at concentrations of 50 to 2000 milligrams can be added to the alginate mix as a fertilizer.

1.d. As an alternative to potassium phosphate, potassium nitrate at concentrations of 300 to 500 millimolar can be added to the alginate mix as a fertilizer.

EXAMPLE G.

(Double Capsules)

1. Calcium Alginate Beads

Calcium alginate beads, made by dropping 3.2% sodium alginate into 100 millimolar calcium chloride, were re-mixed with 3.2% sodium alginate and dropped into 100 millimolar calcium chloride to produce double layered capsules.

2. Superphosphate Alginate Beads 3.2% sodium alginate was complexed as beads in a 0.50 to 1.0% solution of superphosphate fertilizer. The hardened beads were resuspended in 3.2% sodium alginate and complexed as double layer beads in 100 millimolar calcium chloride.

2.a. As an alternative complexing agent for the second complexation, benefin can be used.

Example H (Capsule Storage)

1. Low Temperature Storage

Alfalfa seeds encapsulated as in protocol E.1 but without a herbicide can be stored in a sealed container at $-20°$ C. for at least 14 days without germination. The seeds germinate at 85% of the controls when returned to 25° C.

2. Germination Control with Salt

Tomato seeds, UC82 (Asgrow Seed Co., Lot # VGY 9225, Size 8), encapsulated as in protocol E.1 but without a herbicide can be stored in sealed containers without seed germination for up to one month at ambient temperatures when 0.3 to 0.5 molar sodium chloride is added to the sodium alginate mixture before gelatin. The encapsulated seeds germinated as rapidly and uniformly as controls when placed on agar water or in soil.

2.a. As an alternative to sodium chloride, potassium nitrate can be encapsulated with sodium alginate and seeds at concentrations of 0.30 to 0.50 molar.

2.b. As an alternative seed material, lettuce (Seagreen, lot #H-96-271 HB, USDA, Salinas, Calif.) or petunia (confetti multiflora dwarf color mixture, lot #304, Northrup King) can be encapsulated with germination control.

3. High Osmotic Potentials

Brassica zygotic embryos, encapsulated as in protocol E.1, but without a herbicide, were stored for up to one month in a sealed container by including 12% sucrose in the sodium alginate mixture. The encapsulated zygotic embryos readily germinated as well as controls when placed on Schenk and Hildebrandt medium.

4. Abscisic Acid

The experimental protocol H.3 was duplicated by substituting abscisic acid at concentrations of $10^{-4}$ to $10^{-6}$ millimolar for sucrose.

5. Cool Temperature Storage

The experimental protocols H.3 and H.4 were duplicated by an additional treatment to the capsules of 4° C. storage temperature for one month.

EXAMPLE I (Microorganisms)

1. Encapsulation with Pea and Rhizobia

Thirty seeds of *Pisum sativa*, miragreen variety (Ferry Morse Co.), were mixed with 9 milliliters of sodium alginate plus 6 milliliters of a TY nutrient broth solution (5 grams bactotyptone, 3 grams yeast extract, 15 grams agar per 1000 milliliters water, ref. J. Beringer, "Journal General Microbiology" 84: 188, 1974) containing *Rhizobia legumenosarum*. The concentration of the *Rhizobia* was $2.8 \times 10^8$ per milliliter nutrient broth or $5 \times 10^6$ bacteria per capsule. The capsules containing seeds, bacteria, nutrient broth and sodium alginate were dropped into 100 millimolar calcium chloride and hardened for thirty minutes. The hardened capsules were removed from the calcium chloride, washed with water, and planted in sterile soil in a sealed container. The seeds germinated and vigorous, healthy plants were recovered in 12 days. The *Rhizobia* bacteria population remained at high levels during germination, dropping only to $6 \times 10^5$ bacteria per capsule.

2. Encapsulation with Corn and Azospirillum

The experimental protocol of I.1 was duplicated using *Zea mays* seeds, Goldcrest hybrid (Ferry Morse Co.), instead of Pisum and using Azospirillum strain 242 instead of Rhizobia. The initial Azospirillum concentration was $2.4 \times 10^{10}$ bacteria per milliliter nutrient broth or $4 \times 10^8$ bacteria per capsule. The concentration dropped to $1 \times 10^8$ bacteria per capsule during seed germination.

3. Encapsulation with Lettuce and Bacillus

The experimental protocol of I. 1 was duplicated using *Lactuca sativa* instead of Pisum, using *Bacillus thuringiensis* HD-1 instead of Rhizobia, and L nutrient broth (10 grams bactotyptone, 5 grams yeast extract, 5 grams sodium chloride, 15 grams agar in 1000 milliliters water, ref. E.S. Lennox, "Virology" 1:190, 1955) instead of TY broth. The initial Bacillus concentration was $7.7 \times 10^8$ bacteria per milliliter broth or $1.6 \times 10^5$ bacteria per capsule. The concentration dropped to $1.3 \times 10^4$ bacteria per capsule during seed germination.

3.a. As an alternative microorganism, *Eschericia coli* can replace Bacillus. The initial concentration was $4 \times 10^9$ bacteria per milliliter broth or $6.8 \times 10^7$ bacteria per capsule. The concentration dropped to $1.9 \times 10^4$ bacteria per capsule during seed germination.

4. Encapsulation with Alfalfa and Rhizobia

The experimental protocol of I.1 was duplicated using *Medicago sativa*, Saranac AR FC45002, instead of Pisum and *Rhizobia meliloti* instead of *R. leguminosarum*. The initial *R. meliloti* concentration was $1.5 \times 10^9$ bacteria per milliliter of broth or $2.6 \times 10^7$ bacteria per capsule.

5. Encapsulation with Tomato and Pseudomonas

The experimental protocol of I.3 was duplicated using *Lycopersicum esculentum*, early pak (trade name), instead of lettuce and Pseudomonas sp. KLH76 instead of Bacillus. The initial Pseudomonas concentration was $8 \times 10^6$ bacteria per milliliter broth or $1.4 \times 10^5$ bacteria per capsule.

Although the foregoing invention has been described in some detail by way of illustration and example, for purposes of clarity of understanding, it will be obvious that certain changes and modifications may be practiced within the scope of the appended claims.

I claim:

1. A method for delivering meristematic tissue to an environment for growth and development comprising:
   isolating meristematic tissue substantially free of intact seed coat, which tissue has the potential to differentiate to produce an entire plant body; and
   encapsulating said isolated meristematic tissue together with at least one adjuvant capable of affecting the meristematic tissue, the resulting plant body or the environment, in a hydrated gel capsule.

2. A method as recited in claim 1 wherein said meristematic tissue is selected from the group consisting of somatic-derived meristematic tissue, zygotic tissue and germline tissue.

3. A method as recited in claim 1 wherein said adjuvant is selected from the group consisting of pesticides, herbicides, insecticides, fungicides, fumigants, repellents, rodenticides, fertilizers, nutrients, sugars, carbohydrates, ATP, microorganisms, growth regulators and hormones.

4. A method as recited in claim 1 wherein the meristematic tissue is encapsulated in at least one gel selected from the group consisting of alginate, carrageenan, locust bean gum and gel agents identified in Table 1.

5. A method as recited in claim 1 wherein the meristematic tissue is encapsulated together with at least one adjuvant selected from the group consisting of bensulide, EPTC, metribuzin, pebulate, Prometryn, pronamide, chlorpropham, alachlor, diazinon, superphosphate, calcium phosphate, potassium phosphate, potassium nitrate, calcium nitrate, ammonium nitrate, starch, sucrose, *Rhizobia meliloti*, *Rhizobia leguminosarum*, *Azospirillum*, *Bacillus thuringiensis*, *Eschericia coli* and adjuvants identified in Table 2.

6. A method as recited in claim 1, further comprising encapsulating said meristematic tissue and each of said adjuvants in distinct regions of the gel whereby the adjuvant, tissue and the environment are allowed to interact in a progressive manner.

7. A method as recited in claim 6, wherein each distinct region of the gel matrix comprises a gel agent distinct from the gel agents in adjacent regions.

8. Meristematic tissue substantially free of intact seed coat encapsulated in a hydrated hydrogel capsule together with at least one adjuvant.

9. A meristematic tissue delivery system for delivering totipotent meristematic tissue to an environment for growth and development which comprises:
   isolated meristematic tissue substantially free of intact seed coat having the potential to differentiate to Produce an entire plant body;
   at least one adjuvant in a concentration capable of affecting the meristematic tissue, the plant body or the environment; and
   a hydrated gel matrix encapsulating said meristematic tissue and said adjuvant, whereby said tissue and adjuvant are delivered simultaneously to the environment.

10. A system as recited in claim 9 wherein said meristematic tissue is selected from the group consisting of somatic-derived meristematic tissue, zygotic tissue and germline tissue.

11. A system as recited in claim 9, the gel matrix further comprising distinct regions of the gel matrix containing each adjuvant and the meristematic tissue, whereby the adjuvant, tissue and the environment are allowed to interact in a progressive manner.

12. A system as recited in claim 11 wherein aach distinct region of the gel matrix comprises a gel agent distinct from the gel agents in adjacent regions.

13. A system as recited in claim 9, wherein the meristematic tissue is encapsulated in at least one gel selected from the group consisting of alginate, carrageenan, locust bean gum and gel agents identified in Table 1.

14. A system as recited in claim 9, wherein the meristematic tissue is encapsulated together with at least one adjuvant selected from the group consisting of bensulide, EPTC, metribuzin, pebulate, protetryn, pronamide, chlorpropham, alachlor, diazinon, superphosphate, calcium phosphate, potassium phosphate, potassium phosphate, calcium nitrate, ammonium nitrate, starch, sucrose, *Rhizobia meliloti, Rhizobia leguminosarum, Asospirillum, Bacillus thuringiensis, Eschericia coli* and adjuvants identified in Table 2.

* * * * *

UNITED STATES PATENT AND TRADEMARK OFFICE
CERTIFICATE OF CORRECTION

PATENT NO. : 4,583,320

DATED : April 22, 1986

INVENTOR(S) : M. Keith Redenbaugh

It is certified that error appears in the above—identified patent and that said Letters Patent is hereby corrected as shown below:

```
Col. 1, line 40, "Nutrients" should be --nutrients--.
Col. 6, line 1, insert a dash after "vinylpyridine".
Col. 10, line 48, "Ocalcium" should be --calcium--.
Col. 13, line 64, insert a dash before "benzamide)".
Col. 14, line 51, "with0.01" should be --with 0.1--.
Col. 15, line 31, "(2chloro-2," should be --(2-chloro-2,--.
Col. 18, line 18, "Prometryn" should be --prometryn--.
Col. 18, line 41, "Produce" should be --produce--.
Col. 18, line 58, "aach" should be --each--.
```

Signed and Sealed this

Twenty-second Day of July 1986

[SEAL]

Attest:

DONALD J. QUIGG

Attesting Officer

Commissioner of Patents and Trademarks